United States Patent
Barbes et al.

(10) Patent No.: US 10,371,651 B2
(45) Date of Patent: Aug. 6, 2019

(54) METHOD FOR ANALYZING AN OBJECT BY X-RAY DIFFRACTION

(71) Applicant: Commissariat a L'Energie Atomique et aux Energies Alternatives, Paris (FR)

(72) Inventors: Damien Barbes, Grenoble (FR); Caroline Paulus, Grenoble (FR); Joachim Tabary, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 279 days.

(21) Appl. No.: 15/389,819

(22) Filed: Dec. 23, 2016

(65) Prior Publication Data
US 2017/0184518 A1    Jun. 29, 2017

(30) Foreign Application Priority Data

Dec. 24, 2015 (FR) .................................. 15 63317

(51) Int. Cl.
*G01N 23/207* (2018.01)
*G01N 23/20025* (2018.01)
*G01N 23/20091* (2018.01)

(52) U.S. Cl.
CPC ... *G01N 23/2076* (2013.01); *G01N 23/20025* (2013.01); *G01N 23/20091* (2013.01); *G01N 2223/316* (2013.01)

(58) Field of Classification Search
CPC ......... G01N 23/2076; G01N 23/20025; G01N 23/20091; G01N 2223/316; G01N 23/223

USPC ....................................................... 378/70–89
See application file for complete search history.

(56) References Cited

U.S. PATENT DOCUMENTS

| 6,078,638 A | 6/2000 | Sauer et al. |
| 7,092,485 B2 * | 8/2006 | Kravis .................. G01N 23/20 378/57 |
| 2012/0051517 A1 | 3/2012 | Paulus et al. |
| 2014/0169528 A1 | 6/2014 | Bethke |
| 2014/0348298 A1 | 11/2014 | Ghammraoui et al. |

FOREIGN PATENT DOCUMENTS

| EP | 2 743 687 A2 | 6/2014 |
| WO | WO 2013/098520 A1 | 7/2013 |
| WO | WO 2014/045045 A1 | 3/2014 |

OTHER PUBLICATIONS

French Preliminary Search Report (with Written Opinion) dated Sep. 27, 2016 in French Application 15 63317 filed on Dec. 24, 2015 (with English Translation of Categories of Cited Documents).

* cited by examiner

*Primary Examiner* — Courtney D Thomas
(74) *Attorney, Agent, or Firm* — Oblon, McClelland, Maier & Neustadt, L.L.P.

(57) ABSTRACT

The invention is a method for analysing an object by x-ray diffraction spectroscopy, in which a spectroscopic detector comprising a plurality of adjacent pixels is placed facing an object irradiated by an x-ray beam. Each pixel is able to acquire an energy spectrum of radiation elastically scattered by the object, the radiation propagating in a direction making an acute angle to the propagation direction of the collimated beam. The method allows, on the basis of each measured spectrum, a nature of the materials composing various portions of the object to be determined.

13 Claims, 8 Drawing Sheets

METHOD FOR ANALYZING AN OBJECT BY X-RAY DIFFRACTION

TECHNICAL FIELD

The technical field of the invention is the analysis of an object by spectroscopic analysis of ionising radiation diffracted by said object. The invention is applicable both to the analysis of biological tissues, for diagnostic purposes, and to non-destructive testing in the industrial field or in security-related applications.

PRIOR ART

X-ray diffraction spectroscopy, better known by the acronym EDXRD (energy dispersive x-ray diffraction) is a non-destructive analysis technique used to identify the materials making up an object. This technique is based on elastic scattering of ionising electromagnetic radiation, which is also called Rayleigh scattering. It has already been applied in the detection of explosives or other illicit substances. Generally, this technique consists in irradiating an object using polyenergetic x-ray radiation and in determining the energy spectrum of the radiation backscattered by the object at small angles, typically comprised between 1° and 20°, to the path of the x-ray radiation incident on the object. Analysis of this spectrum allows the constituent materials of the object to be identified. Specifically, most materials have a set spectral signature, depending on their molecular or atomic structure. Comparison of these measured scattering spectra with the signatures of known materials allows the composition of the object to be deduced.

In prior-art devices, a source of irradiation produces polyenergetic x-ray radiation propagating towards an object, a primary collimator, or pre-collimator, being placed between the source and the object, so as to form a finely collimated x-ray radiation beam incident on the object. A second collimator is then placed between the analysed object and a detector, the latter being able to acquire an energy spectrum of the radiation backscattered by the object.

Document WO2013098520 describes a method allowing the spectra of diffracted x-rays emitted by an object to be obtained using a detector including pixels, each pixel being subdivided into what are called virtual pixels. This document presents a method in which the second collimator defines a relatively large aperture, the subdivision into virtual pixels allowing angular resolution to be improved. The combination of spectra obtained with a plurality of adjacent pixels allows spectra of high resolution to be obtained. This method allows the presence of various materials in a given analysed object to be identified, but it does not allow precise spatial information on the composition of the object to be determined. Document WO2016001536 also describes a method allowing to identify a material based on the detection of diffracted x-rays.

The inventors have sought to improve these methods and propose an alternative method for analysing an object, and in particular a composite object, liable to be formed by various materials. This method has an improved spatial resolution, allowing more precise segmentation of the object into elementary volumes, and a reconstruction of the nature of the materials of each of these elementary volumes.

SUMMARY OF THE INVENTION

A first subject of the invention is method for analysing an object according to any one of the appended claims. The method may include the following steps:

a) placing the object facing a source of irradiation emitting ionising electromagnetic radiation and irradiating the object using said source, through a first collimator, so as to form a collimated incident beam propagating towards the object along a propagation axis;

b) placing a detector comprising a plurality of pixels, so that each pixel is able to detect radiation scattered by the object thus irradiated, said scattered radiation propagating in a direction making an acute angle, called the scattering angle, to said propagation axis;

c) acquiring, with a plurality of pixels of the detector, a scattering spectrum representative of an energy distribution of said scattered radiation, each scattering spectrum being associated with one pixel;

d) decomposing the object into elementary volumes and associating, with each pixel, a dispersion function representing a contribution of each elementary volume to the scattered radiation detected by each pixel;

e) on the basis of the acquired scattering spectra and of the dispersion functions associated with each pixel, determining a scattering signature associated with each elementary volume, said signature being representative of a material forming said elementary volume;

f) on the basis of the scattering signatures associated with each elementary volume, estimating a nature of the material forming the various elementary volumes of the object.

According to an embodiment, step e) includes, on the basis of the scattering spectrum acquired by each pixel, determining a scattering function associated with said pixel, said function being obtained by combining said scattering spectrum with a reference spectrum acquired by said pixel while a reference material is placed in the place of the object. The determination of the scattering function associated with each pixel can include taking into account what is called a reference scattering function, which is established, for said pixel, relatively to said reference material. It can also include the establishment of a ratio, term by term, of the scattering spectrum, acquired by said pixel, to said reference spectrum, the ratio being multiplied, term by term, by said reference scattering function established for said pixel. The ratio may be the subject of a change of variable between energy and momentum transfer prior to said term-by-term multiplication.

The reference material is known, and in particular its scattering signature. By scattering signature, what is meant is a distribution of a spectral value, for example a distribution of a momentum transfer or of an energy related data.

According to an embodiment, step e) includes taking into account an attenuation spectral function of the object and an attenuation spectral function of said reference object. The aforementioned ratio may then be multiplied, term by term, by a ratio of the spectral attenuation functions.

According to an embodiment, step e) includes:
- establishing a response matrix on the basis of the scattering functions associated with each pixel;
- establishing a dispersion matrix on the basis of the dispersion functions associated with each pixel;
- estimating a matrix including the scattering signatures of each elementary volume, in such a way that the matrix product of said dispersion matrix by said matrix of scattering signatures of each elementary volume substantially corresponds to said response matrix.

The dispersion function associated with a pixel can be elaborated by placing a calibration object successively in various positions, along said propagation axis, in such way that each position corresponds to an elementary volume of the analysed object, and by carrying out, in each position, the following steps:

irradiating the calibration object and acquiring, with said pixel, a spectrum, called the calibration spectrum, of the radiation scattered by said calibration object placed in said position;

in each calibration spectrum, identifying a calibration peak that is characteristic of said calibration object; and determining the intensity of said calibration peak.

Then, the dispersion function is obtained on the basis of the various intensities of the calibration peaks respectively obtained, for said pixel, in each position of the calibration object. The calibration material of the calibration object may be different than the reference material.

According to one preferred configuration, the detector comprises a plurality of physical pixels, each physical pixel being associated with an electronic processing circuit, each physical pixel being divided into a plurality of virtual pixels. The pixels to which reference was made above are thus virtual pixels.

The method may also comprise one of the following features, implemented alone or in combination:

the radiation scattered by the object and reaching the pixels passes through an aperture of a second collimator, which is placed between the detector and the object, the aperture extending, between the detector and the object, along a median axis that is inclined with respect to the propagation axis of the collimated incident beam. The aperture may especially define an angular range, in such a way that the radiative scatter reaching the detector is emitted at a scattering angle belonging to said angular range, a radiative scatter emitted at an angle out of said angular range being attenuated by said collimator.

The detector extends in a detection plane that is inclined at an angle smaller than 90° to the aforementioned propagation axis.

The spectral attenuation function of the object is obtained by respectively measuring a spectrum of the radiation emitted by the source and a spectrum of the radiation transmitted by the object along said propagation axis.

The object is irradiated by the source of irradiation through a first collimator, so as to form a collimated incident beam propagating towards the object along said propagation axis.

Another subject of the invention is a data storage medium including instructions for the execution of a method such as described in this application, these instructions being executable by a processor.

Another subject of the invention is a device for analysing an object including:

a source of irradiation, able to produce ionising electromagnetic radiation propagating towards a holder able to receive said object;

a first collimator, placed between the source of irradiation and the holder, the first collimator having an aperture able to form a collimated beam propagating along a propagation axis, towards the holder;

a second collimator, placed between the holder and a detector, the second collimator having an aperture extending between said holder and said detector, along a median axis that is inclined with respect to said propagation axis;

the detector comprising pixels, each pixel being able to detect electromagnetic radiation scattered by the object through said aperture, and to acquire an energy spectrum that is called the scattering spectrum;

wherein the device includes a microprocessor able to carry out, on the basis of the scattering spectrum acquired by each pixel, steps d) to f) of the method described herein.

The median axis can make an angle, called the collimating angle, to the propagation axis, this angle being strictly larger than 0° and smaller than 20°.

The device may include an including an auxiliary detector able to acquire a spectrum of radiation transmitted by the object, called the transmission spectrum, held on the holder, along the propagation axis.

Other advantages and features will become more clearly apparent from the following description of particular embodiments of the invention, which are given by way of nonlimiting example and shown in the appended drawings.

SUMMARY OF PARTICULAR EMBODIMENTS

Figure 1A:
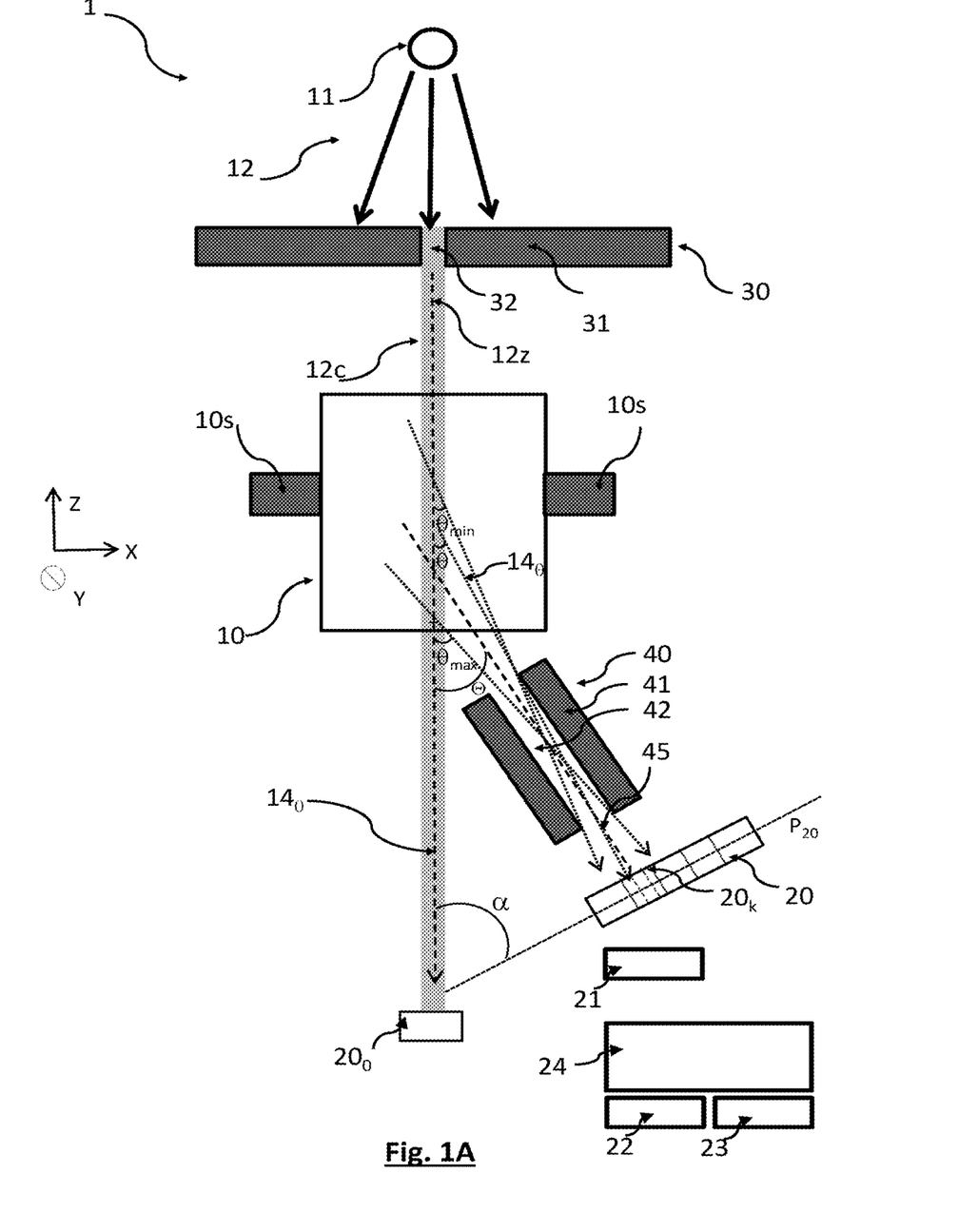
FIG. 1A shows an exemplary device according to the invention.

FIG. 1A shows an exemplary device 1 for analysing an object 10. A source of irradiation 11 emits ionising electromagnetic radiation 12 propagating towards the object 10, the composition of which it is desired to determine. The object 10 is held on a holder $10s$.

The device comprises a first collimator 30, or pre-collimator, able to collimate the radiation emitted by the source of irradiation 11 in order to form a collimated incident beam $12_c$ propagating along a propagation axis $12_z$ towards the object. The device also includes a detector 20, including pixels $20_k$, each pixel being able to detect radiation $14_\theta$ scattered by the object 10, in a direction making a scattering angle $\theta$ to the propagation axis $12_z$. This radiation is for example generated by elastic scattering of the radiation forming the collimated incident beam $12_c$.

The analysing device 1 includes a second collimator 40 that is interposed between the object 10 and the detector 20. This second collimator 40 allows radiative scatter $14_\theta$ scattered by the object 10, at a scattering angle θ to the propagation axis $12_z$ and comprised in an angular range Δθ, to be selectively directed. By selectively directed, what is meant is that radiation scattered at an angle not comprised in this angular range Δθ is attenuated by the second collimator.

The analysing device 1 is placed in a frame of reference with which an orthogonal coordinate system X, Y, Z such as shown in FIG. 1A is associated.

The term ionising electromagnetic radiation designates electromagnetic radiation made up of photons of energy higher than 1 keV and preferably lower than 5 MeV. The energy range of the ionising radiation may be comprised between 1 keV and 2 Mev, but it most often extends between 1keV and 150 keV or 300 keV. The ionising radiation may be x-ray or γ radiation. Preferably, the source of ionising radiation is polyenergetic, the incident radiation being emitted in an energy range generally extending over several tens or even hundreds of keV. It is especially a question of an x-ray tube.

The source of irradiation 11 is an x-ray tube equipped with a tungsten anode that is subjected to a voltage, generally comprised between 40 and 170 kV, that it is possible to vary in order to modify the energy range of the incident radiation 12. The detector 20 includes pixels $20_k$ distributed in a row or in a two-dimensional matrix array, each pixel extending over an area of 2.5 by 2.5 $mm^2$, its thickness being 5 mm. The material forming each pixel is a semiconductor, for example CdTe or CdZeTe, or any other material suitable for performing spectroscopic measurements, preferably at room temperature. It could also be a scintillator material, providing its energy resolution is high enough. The detector is resolved in energy, and each pixel allows spectra to be obtained in channels with an energy resolution of about 1 keV. The source of irradiation 11 may include a metal screen, for example made of copper, so as to block the propagation, towards the pre-collimator 30, of radiation the energy of which is lower than 20 keV. When this screen is made of copper, its thickness is for example equal to 0.2 mm.

The first collimator 30, or pre-collimator, includes a block of dense material 31, for example including tungsten, able to absorb almost all the radiation 12 emitted by the source of irradiation 11. It includes a narrow aperture 32, extending along an axis, which is called the propagation axis $12_z$, allowing a narrow collimated beam $12_c$ to pass. By narrow aperture, what is meant is an aperture the diameter or largest diagonal of which is smaller than 2 cm or even than 1 cm. In this example, the aperture is a cylinder of 1 mm diameter.

The object 10 may be an industrial part the quality or composition of which is desired to determine. It may also be a piece of luggage that it is desired to inspect. The device 1 is then used for non-destructive testing/inspection purposes. It may also be a question of a living biological tissue, for example a body part of an animal or of a human being. The device is then a medical analysis device used with the purpose of aiding diagnosis. The body part may in particular be an organ in which, following a first examination, for example a radiograph or a scan, an anomaly, in particular a cancerous tumour, is suspected to be present.

The second collimator 40 includes walls 41 made of a dense material and able to absorb almost all the radiation $14_\theta$ scattered by the object outside of the aforementioned angular range. An aperture in said dense material defines a channel 42 extending along a median axis 45. By median axis, what is meant is an axis extending, along the channel, at equal distance from the walls bounding the channel. This median axis 45 is inclined with respect to the propagation axis $12_z$ of the collimated incident beam $12_c$. The angle ⊖ between the median axis 45 of the channel 42 and the propagation axis $12_z$, which is what is called the collimating angle, is strictly larger than 0° and smaller than 20°. The collimator is thus able to transmit, towards the detector 20, scattered radiation $14_\theta$ propagating at an angle, called the scattering angle θ, in a defined angular range Δθ about the collimating angle ⊖. FIG. 1A shows two radiative scatters $14_\theta$ bounding the field of observation Δθ of the second collimator 40, their respective scattering angles being the limits $\theta_{min}$ and $\theta_{max}$ of the angular range associated with the second collimator 40. The length of each channel is typically comprised between 50 and 100 mm, whereas the aperture is a few hundred microns, for example 500 μm, in size in a direction perpendicular to the median axis 45.

In the embodiment shown in FIG. 1A, the second collimator 40 includes only a single channel 42. According to other embodiments, the collimator 40 may include a plurality of channels $42_n$, which may for example be placed parallel to one another, each channel being associated with a collimating angle $\ominus_n$ and an angular range $\Delta\theta_n$.

The radiation detector is a detector comprising pixels $20_k$ that are arranged in a plane called the detection plane $P_{20}$. The index k designates a coordinate of each pixel in the detection plane $P_{20}$. The pixels may be arranged in a row but in general they will be arranged in a regular two-dimensional matrix array. In the example described in this application, the detection plane $P_{20}$ extends in a direction making an angle α strictly smaller than 90° to the propagation axis $12_z$ of the collimated incident radiation $12_c$. This angle α is preferably comprised between 70° and 88° or 89°. Preferably, the detection plane $P_{20}$ is orthogonal to the median axis 45 of the channel 42 of the second collimator 40.

Each pixel $20_k$ of the radiation detector 20 includes:
- a detector material able to interact with the photons of scattered radiation $14_\theta$ transmitted by the object 10 through the second collimator 40, this material being a scintillator material or, preferably, CdTe or CdZnTe i.e. a semiconductor material compatible with use at room temperature;
- an electronic circuit 21 able to generate a signal the amplitude A of which depends, and is preferably proportional, to an energy E deposited by each photon interacting with the detector material; and
- a spectroscopy circuit able to establish an energy spectrum, denoted $S_k^E$, of the signals detected during a time period called the period of acquisition.

Thus, each pixel $20_k$ is able to produce a spectrum $S_k^E$ of the radiation $14_\theta$ scattered by the object during a time period during which the object is irradiated by the source of irradiation.

The term energy spectrum designates a histogram of the amplitude A of the signals detected during a period of acquisition of the spectrum. A relationship between the amplitude A of a signal and the energy E of the radiation may be obtained via an energy calibration function g such that E=g(A), according to principles known to those skilled in the art. An energy spectrum $S_k^E$ may therefore take the form of a vector, each term $S_k^E(E)$ of which represents an amount of radiation detected by the pixel $20_k$ in an energy range $$E \pm \frac{\partial E}{2},$$

where ∂E is the spectral width of an energy discretisation interval, or channel, of the spectrum.

The device also comprises a computational unit, or processor 22, for example a microprocessor, able to process each spectrum $S_k^E$ acquired by the pixels $20_k$ of the detector 20. In particular, the processor is a microprocessor connected to a programmable memory 23 in which a sequence of instructions for carrying out the spectra-processing operations and computations described in this description are stored. These instructions may be saved on a storage medium that is readable by the processor, such as a hard disk, a CD-ROM or another type of memory. The processor may be connected to a display unit 24, a screen for example.

Each pixel $20_k$ is connected to an electronic circuit 21 allowing signals representative of the energy of the radiative scatter transmitted by the collimator 40 to be collected. The electronic circuit 21 may be connected to the processor 22 that was described above, allowing initial processing, consisting in analysing the signals emitted by a plurality of adjacent pixels, to be carried out so as to locate the point of impact of the detected radiation with a spatial resolution lower than the pitch with which these pixels are distributed. Such processing, which is known to those skilled in the art as sub-pixelation or sur-pixelation, amounts to forming what are called virtual pixels $20'_k$, the area of each virtual pixel possibly for example being 0.5 mm×0.5 mm or even 0.1 mm×0.1 mm. In this example, the size of each virtual pixel is 150 µm×150 µm. Thus, the spatial resolution of the detector 20 is increased. Such a decomposition of virtual pixels is known to those skilled in the art. It has already been described in the publication Warburton W. K, "An approach to sub-pixel spatial resolution in room temperature X-ray detector arrays with good energy resolution" and in Montemont et al. "Studying spatial resolution of CZT detectors using sub-pixel positioning for SPECT", IEEE transactions on nuclear science, Vol. 61, No. 5, October 2014.

In the rest of the text, when pixels $20_k$ are referred to, it may either be virtual pixels or physical pixels that are being referred to. Preferably, it will be a question of virtual pixels because the best detector spatial resolution is obtained in this way.

The device 1 preferably includes a detector that is what is called an auxiliary detector $20_0$ placed in what is called a transmission configuration, which detector is able to detect not radiation scattered by the object held on the holder, but radiation $14_0$ transmitted by the object 10 along the propagation axis $12_z$. Such radiation, which is what is called radiative transmission, is transmitted by the object 10 without having interacted with the latter. The auxiliary detector $20_0$ allows a spectrum $S_0^E$ of the radiation $14_0$ transmitted by the object 10, in the propagation direction $12_z$ of the collimated incident beam $12_c$, to be established. Such a spectrum may be used to determine an attenuation spectral function Att of the object, as is described below.

Figure 1B:
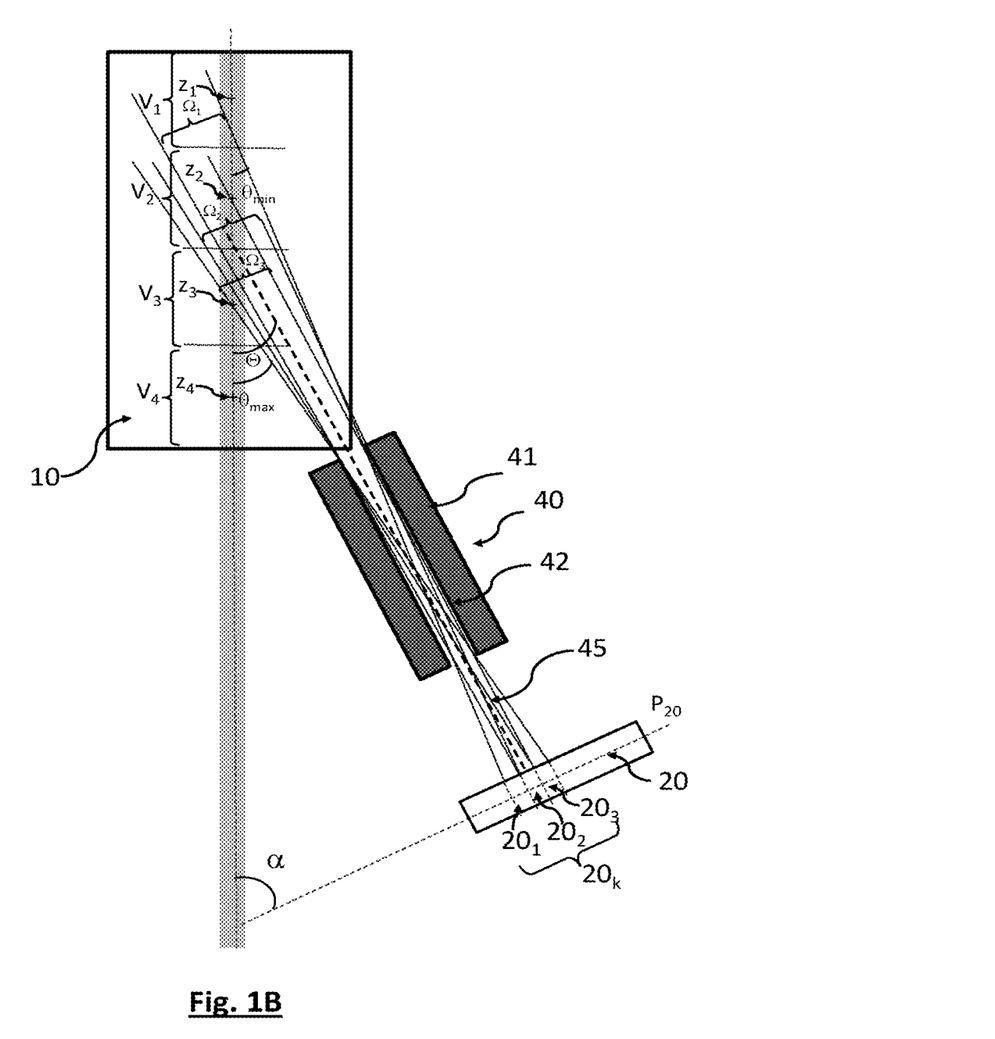
FIG. 1B shows a detail of FIG. 1A, illustrating the field of observation of each pixel and the decomposition of the object into elementary volumes.

FIG. 1B shows more precisely the object 10 and the field of observation conferred by the second collimator 40. In this figure, three pixels $20_1$ . . . $20_3$ able to receive scattering radiation $14_\theta$ may be seen, one field of observation $\Omega_1$, $\Omega_2$, $\Omega_3$ being associated with each pixel. The field of observation of each pixel is defined by the size of said pixel and by the geometry of the collimator 40. The object may moreover be regularly or irregularly sampled into a plurality of elementary volumes $V_1 \ldots V_{NZ}$, each elementary volume $V_z$ being associated with a coordinate z along the propagation axis $12_z$. $N_Z$ designates the number of elementary volumes $V_z$ considered. FIG. 1B shows four elementary volumes $V_1$, $V_2$, $V_3$, $V_4$, centred on coordinates $z_1$, $z_2$, $z_3$, $z_4$ along the propagation axis, respectively. The basic idea of the invention is to estimate the nature of the material from which the object 10 is made in each of these elementary volumes, by implementing a reconstruction algorithm such as described below. Because of the aperture of the collimator 40, a given elementary volume $V_z$ may emit scattered radiation towards various pixels $20_k$ of the detector, in particular when the detector is subdivided into virtual pixels the size of which is small. The scattering spectrum measured by each pixel results from the detection of radiation scattered, at various scattering angles, by various elementary volumes of the object. Sampling the field of observation of each pixel into independent elementary volumes allows the object to be reconstructed on the basis of a fine sampling thereof, said sampling being arbitrarily defined.

During the analysis, the object 10 is irradiated by the polyenergetic incident beam $12_c$. Under the effect of the Rayleigh elastic scattering, some of the incident radiation $12_c$ is scattered in a plurality of directions, the intensity of a radiative scatter possibly being more or less high depending on the pair formed by the energy of the photons and the scattering direction. This intensity variation as a function of the scattering angle θ forms the scattering signature, which is specific to each material. In the case of a crystal, the scattering intensity is nonzero only in precise energy-of-the-incident-photon/scattering-angle pair configurations defined by the Bragg equation:

$$2d\sin\left(\frac{\theta}{2}\right) = n\frac{hc}{E} \qquad (1)$$

where:
d is a characteristic distance of the molecular or atomic arrangement of a component material of the irradiated object. When the analysed material is a crystal, d corresponds to the inter-reticular distance;
n is an integer designating the order of the interference;
E designates the energy of the scattered radiation, expressed in keV;
θ designates the scattering angle; and
h and c designate Planck's constant and the speed of light, respectively.

It is common to express a quantity, designated by the term momentum transfer, represented by the letter χ and expressed in $nm^{-1}$, such that:

$$\chi = \frac{\sin\left(\frac{\theta}{2}\right)E}{hc} \qquad (2)$$

To each pixel or virtual pixel $20_k$ of the detector 20 corresponds a scattering angle $\theta_k$ representing the most probable angle at which a radiative scatter $14_\theta$ reaching the pixel will have propagated. The advantage of sur-pixelation is that pixels of small size are obtained, thereby decreasing the angular range of the radiative scatters liable to reach one thereof.

Figure 2:
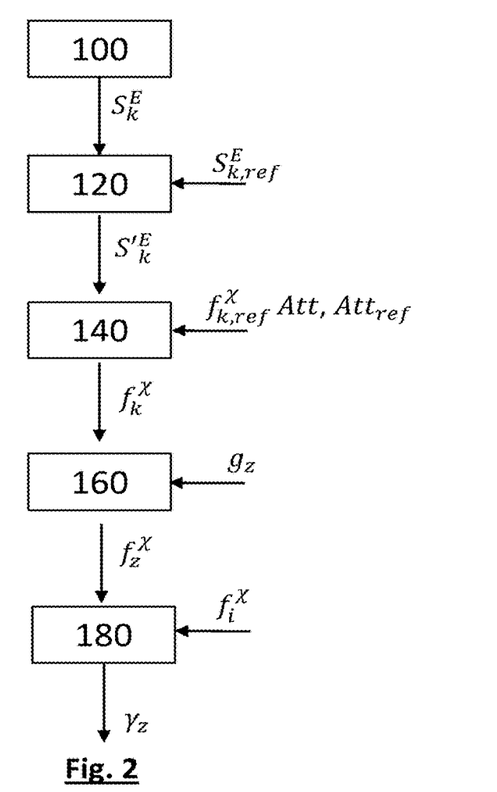
FIG. 2 shows the main steps of an analysing method according to one embodiment of the invention.

The main steps of a method for analysing the object 10 will now be described with reference to FIG. 2.

In a first step 100, the object 10 is irradiated by the source of irradiation 11 and each pixel $20_k$ of the detector 20 acquires a spectrum $S_k^E$ of the radiative scatter $14_\theta$ to which it is exposed. In the example, the collimating angle $\Theta$ may be comprised between 1° and 20°. The exponent E represents the fact that the spectrum is here a function of energy. Since the scattering angle $\theta_k$ associated with each pixel $20_k$ is known, it is possible to express a scattering function not as a function of energy but as a function of the momentum transfer $\chi$ by performing a change of variable according to the Equation (2), in which case the spectrum is denoted $S_k^\chi$.

Figure 1C:
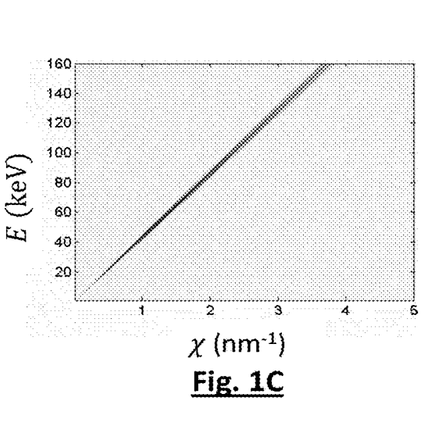
FIGS. 1C and 1D show what are called angular response matrices associated with a pixel.

The energy spectrum may be expressed according to the following equation:

$$S_k^E = D_k \cdot (S_{inc} \times Att \times (A_k f_k^\chi)) \quad (3)$$

where:
- $S_k^E$ is the energy spectrum measured by the pixel $20_k$, of size $(N_E, 1)$; $N_E$ designates the number of channels of the spectrum, i.e. the number of energy discretisation intervals.
- $D_k$ Is a response matrix of the pixel $20_k$, representing the imperfections of the detection. Each term $D_k(E, E_i)$ of this matrix represents a probability that a photon incident on the detector, and of energy $E_i$, is considered by the detector to have an energy E. This matrix is here a square matrix of $N_E \times N_E$ size;
- $S_{inc}$ is an energy spectrum of the collimated incident beam $12_c$, of dimension $(N_E, 1)$;
- Att is a vector, called the attenuation spectral function, representing an attenuation of the incident spectrum by the object 10 and of dimension $(N_E, 1)$;
- $A_k$ is a matrix representing an angular response function of each pixel $20_k$, of size $(N_E, N_\chi)$, where $N_\chi$ represents the number of discretisation intervals of the momentum transfer $\chi$. Each term $A_k(E, \chi)$ represents a probability that the energy of a photon of energy E detected by a pixel $20_k$ corresponds to a momentum transfer equal to $\chi$, given Equation (2). The application of this matrix allows a change of variable to be performed between a spectrum, measured by said pixel and expressed as a function of energy E, and the same spectrum expressed as a function of momentum transfer $\chi$. FIG. 1C is an illustration of this matrix, the maximum terms of which are located on a line defined by the equation $$E = \frac{hc\chi}{\sin\left(\frac{\theta_k}{2}\right)}, \quad (4)$$

where $\theta_k$ represents the average scattering angle associated with the pixel $20_k$ in question. Such a matrix is defined for each pixel $20_k$;
- $f_k^\chi$ is a scattering function associated with each pixel $20_k$. It is a spectrum of the values of the momentum transfer $\chi$ measured by said pixel $20_k$. This scattering function depends only on the materials present in the elementary volumes $V_z$ lying in the observation field $\Omega_k$ of said pixel $20_k$. The dimension of $f_k^\chi$ is $(N_\chi, 1)$;
- × designates the Hadamard product (term-by-term product) and · designates the matrix product.

Figure 1D:
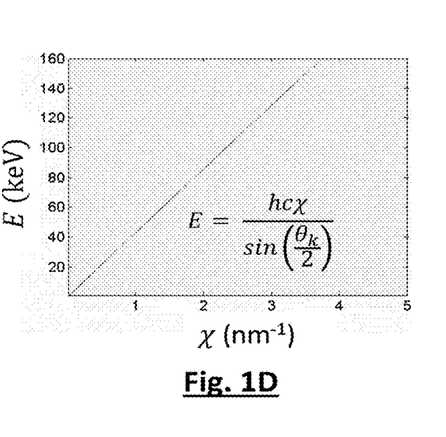

The recourse to pixels of small size, whether they be physical or virtual pixels, allows the field of observation of each pixel to be limited. Thus, in this example, the angular response matrix $A_k$ may be considered to be a diagonal matrix representing a bijective function expressing a change of variable, with $A_k(E, \chi) = 1$ when $$E = \frac{hc\chi}{\sin\left(\frac{\theta_k}{2}\right)},$$

this diagonal matrix being shown in FIG. 1D.

Moreover, in this example, the energy resolution of the detector is considered to be good enough for the response matrix $D_k$ of each pixel $20_k$ to be considered to be the identity matrix.

Equation (3) then becomes:

$$S_k^E = S_{inc} \times Att \times f_k^E \quad (5)$$

where $f_k^E$ designates the scattering function measured by each pixel $20_k$ as a function of energy. On the basis of this scattering function, expressed as a function of the energy E, it is possible to establish an estimated scattering function $f_k^\chi$ that is a function of momentum transfer $\chi$, the passage between the vectors $f_k^E$ and $f_k^\chi$ being established by the application of the aforementioned matrix $A_k$, with $f_k^E = A_k \cdot f_k^\chi$.

In steps 120 and 140, a reference scattering spectrum $S_{k,ref}^E$ obtained for each pixel $20_k$ while a reference object $10_{ref}$ made of a known material is placed in the place of the object 10 is considered. The scattering properties of the reference object are known. It is then possible to establish a reference scattering function $f_{k,ref}^E$, $f_{k,ref}^\chi$ associated with each pixel $20_k$. The way in which this reference scattering function is obtained will be detailed below. Assuming that the spectrum $S_{inc}$ of the collimated incident beam $12_c$ does not change between the measurement of the scattering spectrum $S_{k,ref}^E$ of the reference object and the measurement of the scattering spectrum $S_k^E$ of the analysed object, the spectrum of the radiation scattered by each pixel $20_k$ may be expressed as follows.

$$S_{k,ref}^E = S_{inc} \times Att_{ref} \times f_{k,ref}^E \quad (6),$$

where $Att_{ref}$ designates an attenuation spectral function of the reference object $10_{ref}$.

It is then possible to form a scattering spectrum, denoted $S'_k^E$, that is normalised by said reference scattering spectrum $S_{k,ref}^E$ and such that:

$$S'_k^E = \frac{S_k^E}{S_{k,ref}^E} = \frac{Att \times f_k^E}{Att_{ref} \times f_{k,ref}^E}. \quad (7)$$

This normalisation constitutes step 120. On the basis of this normalised spectrum, it is possible to determine a scattering function $f_k^\chi$ for each pixel $20_k$, this constituting step 140, according to the expression:

$$f_k^\chi = f_{k,ref}^\chi \times A_k^{-1} \cdot \left[ \frac{S'_k^E \times Att_{ref}}{Att} \right], \quad (8)$$

where $f_{k,ref}^\chi$ designates the reference scattering function associated with the pixel and expressed as a function of momentum transfer. Thus, since $Att_{ref}$, $f_{k,ref}^\chi$ and Att are known and $S_k^E$ has been measured, it is possible to estimate $f_k^\chi$ using expression (8).

In a step 160 it is sought to obtain a scattering signature representative of each elementary volume of the object on the basis of the scattering functions $f_k^\chi$ respectively obtained from each pixel $20_k$. Specifically, on account of the angular aperture of the collimator 40, radiation scattered at various angles and respectively generated by various elementary volumes may be detected by one and the same pixel $20_k$.

This spatial dispersion is characterised by a dispersion function, which is called the intensity spatial dispersion function and denoted $g_k$, representing the intensity of radiation scattered by an elementary volume $V_z$ centred on a coordinate z, and reaching a pixel $20_k$.

This dispersion function $g_k$ is established for each pixel $20_k$. The way in which this dispersion function $g_k$ is established will be described below.

A dispersion matrix G may be constituted, each row of which is formed by the various values of the dispersion function $g_k$ associated with a pixel $20_k$, as a function of z. Each term G(k,z) of the matrix G represents the intensity of a radiative scatter detected by a pixel $20_k$ and originating from an elementary volume $V_z$ centred on z. In other words, $G(k, z)=g_k(z)$.

Step 160 amounts to taking into account this dispersion by constituting a matrix $F_k$, each row of which represents a scattering function $f_k^\chi$ obtained by a pixel $20_k$. Each term $F_k(k, \chi)$ of this matrix represents a value of the scattering function $f_k^\chi$ measured at one value of $\chi$ by a pixel $20_k$. The dimension of this matrix is $(N_k, N_\chi)$, where $N_k$ designates the number of pixels.

It is sought to form a matrix $F_z$ of scattering signatures of the object 10, each row of which represents a scattering signature $f_z^\chi$ relative to an elementary volume $V_z$ centred on z. Each term $F_z(z, \chi)$ of this matrix represents a value of the scattering signature (or form factor) at the value $\chi$, of an elementary volume $V_z$. The dimension of this matrix is $(N_z, N_\chi)$, where $N_z$ designates the number of elementary volumes $V_z$ considered.

The dispersion matrix G establishes a relationship between the scattering functions $f_k^\chi$ of each pixel, forming the matrix $F_k$, and the scattering signatures of each elementary volume $f_z^\chi$ forming the matrix $F_z$, such that: $F_k = G \cdot F_z$ (9).

It is then a question, on the basis of the measurements collected at the level of each pixel, of obtaining a piece of information characterising the radiation scattered by each elementary volume.

Having determined the dispersion matrix G, and having formed, on the basis of the measurements, the matrix of the scattering functions $F_k$, it is possible to obtain an estimation of the matrix of the scattering signatures $F_z$ using an inversion algorithm. Among commonly used iterative inversion algorithms, a maximum likelihood expectation maximisation or MLEM algorithm may be used. According to such an algorithm, the value of each term of the matrix $F_z$ may be estimated using the following expression:

$$\hat{F}_z^n(z, \chi) = \hat{F}_z^{n-1}(z, \chi) \frac{1}{\Sigma_k G(k, z)} \Sigma_k \frac{F_k(k, \chi) \cdot G(k, z)}{\Sigma_z G(k, z) \cdot \hat{F}_z^{n-1}(z, \chi)} \quad (10)$$

the exponent n designating the rank of each iteration. Each iteration allows an estimation $\hat{F}_z^n$ of the matrix $F_z$ to be obtained.

The iterations are repeated until a convergence criteria is met, the latter possibly being a preset number of iterations, or a small variation between the values estimated in two successive iterations. Implementation of this algorithm assumes a step of initialising the matrix $F_z$. For example, this initialisation is such that:

$$F_z^{n=0} = \begin{bmatrix} 1 & \cdots & 1 \\ \vdots & \ddots & \vdots \\ 1 & \cdots & 1 \end{bmatrix} \quad (11)$$

At the end of step 160, an estimation of the matrix $F_z$ is obtained, each row of which represents a scattering signature $f_z^\chi$ of a constituent material of an elementary volume $V_z$ of the object 10.

In a step 180, the material forming each elementary volume $V_z$ is identified from the scattering signature $f_z^\chi$ that is associated therewith. To do this, standard scattering signatures $f_i^\chi$ of various known standard materials 10i are provided. The standard scattering signatures are either established experimentally, or obtained from the literature. The proportions $\gamma_z(i)$ of the material 10i in the elementary volume $V_z$ may be determined by the expression:

$$(\gamma_z(i=1) \ldots \gamma_z(i=N_i)) = \text{Argmin}(\|f_z^\chi - \Sigma_i \gamma_z(i) f_i^\chi\|^2) \quad (12)$$

where $N_i$ designates the number of known standard materials 10i.

A vector $\gamma_z$, each term $\gamma_z(i)$ of which represents a proportion of the material 10i in the elementary volume $V_z$, is obtained.

Obtaining the Dispersion Functions in the Scattering Matrix G

The passage between the scattering functions $f_k^\chi$ measured by a pixel and the scattering signatures $f_z^\chi$ of the radiation emitted by an elementary volume $V_z$ requires the use of dispersion functions $g_k$, which were mentioned above and which are associated with each pixel $20_k$, on the basis of which it is possible to establish the dispersion matrix G. These functions may be obtained by simulation using computational codes. It is also possible to determine them experimentally, using a calibration object $10_c$ constituted by a known material taking the form of a thin plate, able to be successively moved along the propagation axis $12_z$ of the collimated incident beam $12_c$. By thin plate, what is meant is a width of about that of an elementary volume, i.e. of about the spatial resolution that it is desired to obtain.

Figures 3A, 3B:
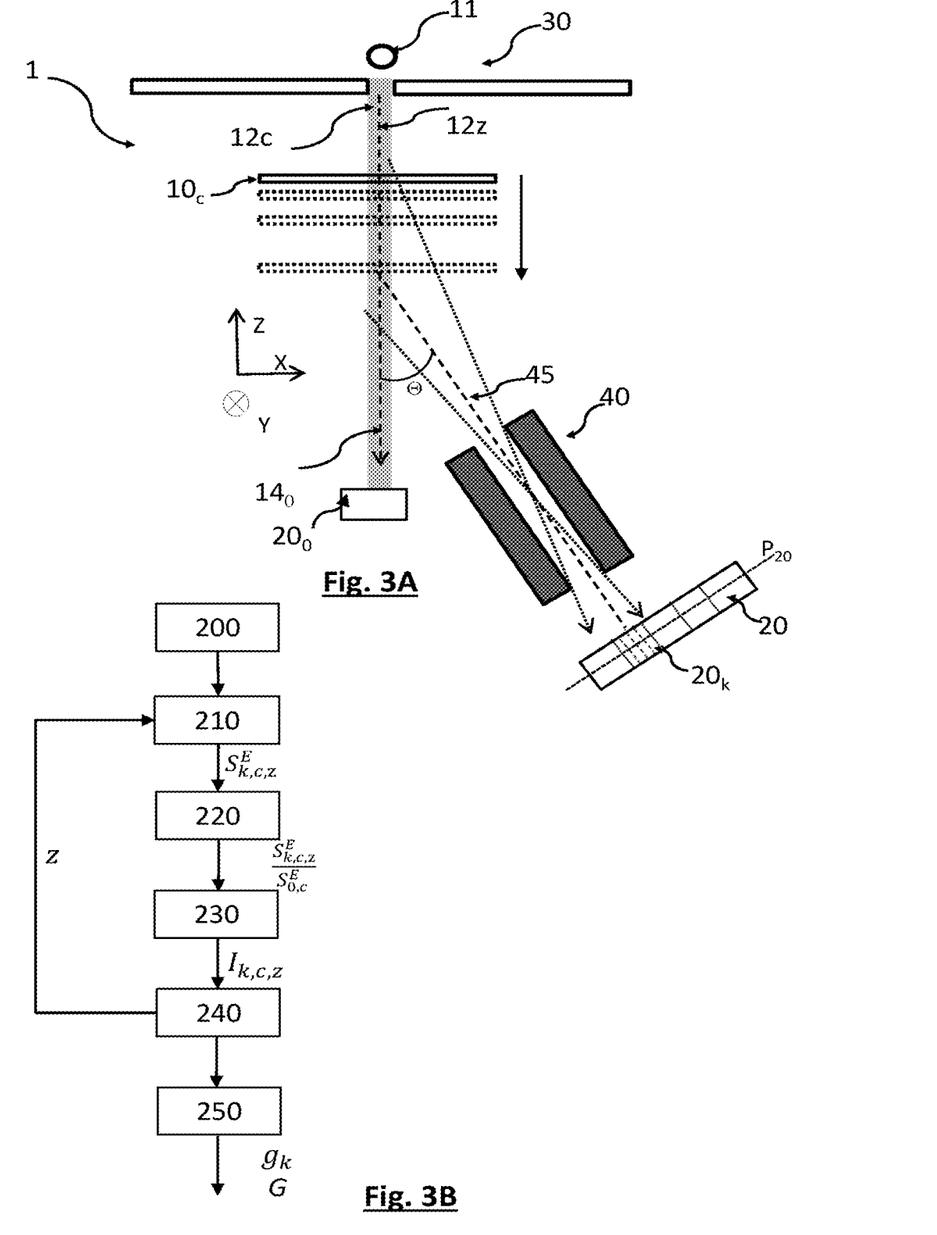
FIG. 3A shows a device allowing a dispersion function to be obtained.
FIG. 3B illustrates the main steps of a method allowing such a function to be obtained.

FIG. 3A shows a device allowing the dispersion functions $g_k$ of each pixel to be obtained, in association with the main steps of the method, which are illustrated in FIG. 3B. The calibration object $10_c$ is translated along the axis $12_z$ so as to successively occupy the various elementary volumes $V_z$ of an analysed object. In each position z of the calibrating object $10_c$, the latter is irradiated by the source of irradiation 11 and each pixel $20_k$ acquires a calibration spectrum $S_{k,c,z}^E$ of the radiation scattered when the calibration object $10_c$ occupies a position z.

The calibration object $10_c$ is chosen so as to have a scattering signature having characteristic peaks. It is for example possible to choose aluminium, of 3 mm thickness, having a characteristic distance at 2.0248 Å. This corresponds to a momentum transfer at $\chi=2.469$ nm$^{-1}$. The thickness of the calibration object must be consistent with the sought-after spatial resolution. It may for example be comprised between 1 mm and 1 cm if it is desired to obtain a spatial resolution of better than 1 cm.

Figure 3C:
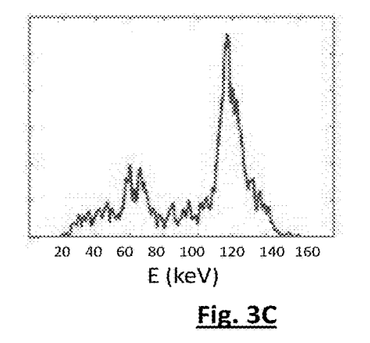
FIGS. 3C and 3D show an exemplary spectrum containing a characteristic scattering peak called the calibration peak, respectively before and after a normalisation with a transmission spectrum. These spectra allow the intensity of said peak to be determined and thus the dispersion function to be derived.
Figure 3D:
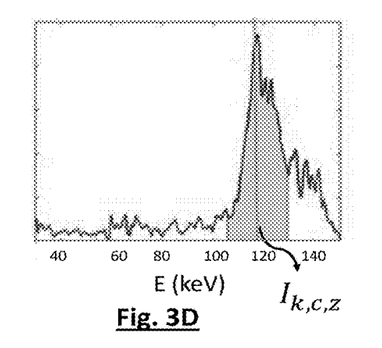

Let us for example consider a pixel $20_k$ configured to essentially receive a radiative scatter emitted at an angle $\theta$ of 2.5°. FIG. 3C shows a spectrum $S_{k,c,z}^E$ of the scattered radiation acquired by this pixel. This spectrum may be normalised by a transmission spectrum $S_{0,c}^E$ measured by the auxiliary detector $20_0$, placed in transmission, in order to obtain a normalised spectrum as shown in FIG. 3D. The transmission spectrum $S_{0,c}^E$ corresponds to a spectrum of radiation having passed through the calibration object $10_c$ parallelly to the propagation axis $12_z$, without having interacted with the calibration object $10_c$. A peak, called the calibration peak, which is centred on an energy of 120 keV, is observed, this being in accordance with the energy E obtained with Equation (2) if $\chi=2.469\text{nm}^{-1}$ and $\theta=2.5°$. The calibration peak extends below and above 120 keV because of the energy and angular resolution of the pixel $20_k$. Its integral $I_{k,c,z}$, shown in FIG. 3D, may easily be obtained using one of the spectrum processing algorithms conventionally used in the field of spectroscopy. It represents the amount of radiation detected by the pixel $20_k$ in the calibration peak when the calibration object is placed in a position z. In each position z of the calibration object $10_c$, the integral $I_{k,c,z}$ of the calibration peak is determined from the scattering spectrum $S_{k,c,z}^E$, which is preferably normalised by the transmission spectrum $S_{0,c}^E$. The dispersion function $g_k$ associated with each pixel $20_k$ then includes, for all of the positions z, the integral $I_{k,c,z}$ of the calibration peak. In other words: $g_k(z) = I_{k,c,z}$ (13).

Thus, intensity values $I_{k,c,z}$ representing an amount of photons detected by a pixel $20_k$, in a peak representative of the calibration object, when the latter occupies a position z in the object, i.e. occupies an elementary volume $V_z$ centred on z, are obtained.

Figure 3E:
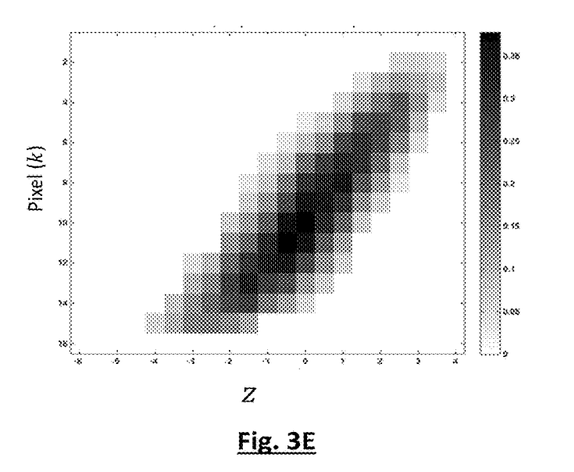
FIG. 3E shows a dispersion matrix, each row of which represents one dispersion function.

It is possible then to establish the dispersion matrix G, such as shown in FIG. 3E, each term of which $G(k,z)=g_k(z)=I_{k,c,z}$. This matrix represents the intensity of the scattered radiation detected by a pixel $20_k$ originating from an elementary volume $V_z$ of the object centred on z. It is of dimension $(N_k, N_z)$. Each row k of this matrix represents a dispersion function $g_k$ of a pixel $20_k$ associated with said row. The values of the intensities $I_{k,c,z}$ are expressed on a greyscale.

Thus, the determination of the dispersion matrix comprises the following steps:
  placing the calibration object $10_c$, constituted of a known material, in a position z, in the field of observation of the second collimator (step 200);
  at said position z, measurement of the scattering spectrum $S_{k,c,z}^E$ by the pixels $20_k$ of the detector 20 (step 210);
  normalisation of each scattering spectrum by a transmission spectrum $S_{c,0}^E$ measured through the calibration object by the auxiliary detector $20_0$ (step 220), this normalisation being optional but preferable;
  in each scattering spectrum thus normalised, determining the intensity $I_{k,c,z}$ of a calibration peak representative of the constituent material of the calibration object (step 230);
  reiterating steps 210 to 230 while moving the calibration object successively to various positions z in the field of observation of the second collimator (step 240); and
  using the intensities, obtaining the scattering function $g_k$ associated with each pixel and the dispersion matrix G (step 250).

At certain positions z of the calibration object $10_c$, the calibration spectrum $S_{k,c,z}^E$ measured by a pixel $20_k$ may not include an identifiable calibration peak. In this case, this calibration spectrum is not taken into account to determine the dispersion function associated with the pixel.

Obtaining the Scattering Function $f_{k,ref}^\chi$ of the Reference Material, for Each Pixel $20_k$.

Step 160 requires the scattering function $f_{k,ref}^\chi$ of each pixel $20_k$ to be known when a radiative scatter originating from the reference material $10_{ref}$ is detected. In the presence of such a material, occupying all of the elementary volumes $V_z$ in the field of observation of the second collimator 40, the scattering signature $f_{z,ref}^\chi$ of each elementary volume $V_z$ corresponds to a scattering signature $f_{ref}^\chi$ of the reference material, which signature is known and common to all of the elementary volumes. The scattering function $f_{k,ref}^\chi$ of each pixel is obtained according to the Expression (9), by constituting a matrix $F_{Z,ref}$ each row of which corresponds to the scattering signature $f_{ref}^\chi$ of the reference material $10_{ref}$. A matrix $F_{k,ref} = G \cdot F_{Z,ref}$ (14) is obtained, each row of the matrix $F_{k,ref}$ representing the scattering function f associated with each pixel $20_k$, of the reference object $10_{ref}$.

Obtaining the Attenuation Spectral Functions

The method preferably assumes the use of the attenuating spectral functions Att and $\text{Att}_{ref}$ representing the attenuation of the collimated incident beam $12_c$ by the object 10 and by the reference object $10_{ref}$ respectively. These functions are respectively obtained using the auxiliary detector $20_0$, placed in transmission, the latter measuring:
  an energy spectrum $S_{inc}$ of the collimated incident beam $12_c$, this spectrum being obtained with no object placed between the detector $20_0$ and the first collimator 30;
  an energy spectrum $S_0^E$ or $S_{0,ref}^E$ of the radiation $14_0$ transmitted, along the propagation axis $12_z$, by the object 10 or the reference object $10_{ref}$. This transmitted radiation does not undergo interaction with the object (or with the reference object).

Having acquired these spectra, it is possible to define an attenuation spectral function by a comparison, generally taking the form of a ratio. Thus, the attenuation Att of the object 10 is obtained by a ratio between $S_{inc}$ and $S_0^E$, and the attenuation $\text{Att}_{ref}$ of the reference object is obtained by a ratio between $S_{inc}$ and $S_{0,ref}^E$. This corresponds to the following equations:

$$Att = \frac{S_{inc}}{S_0^E}; \quad (15)$$

$$Att_{ref} = \frac{S_{inc}}{S_{0,ref}^E} \quad (16)$$

Trial

Figure 4A:
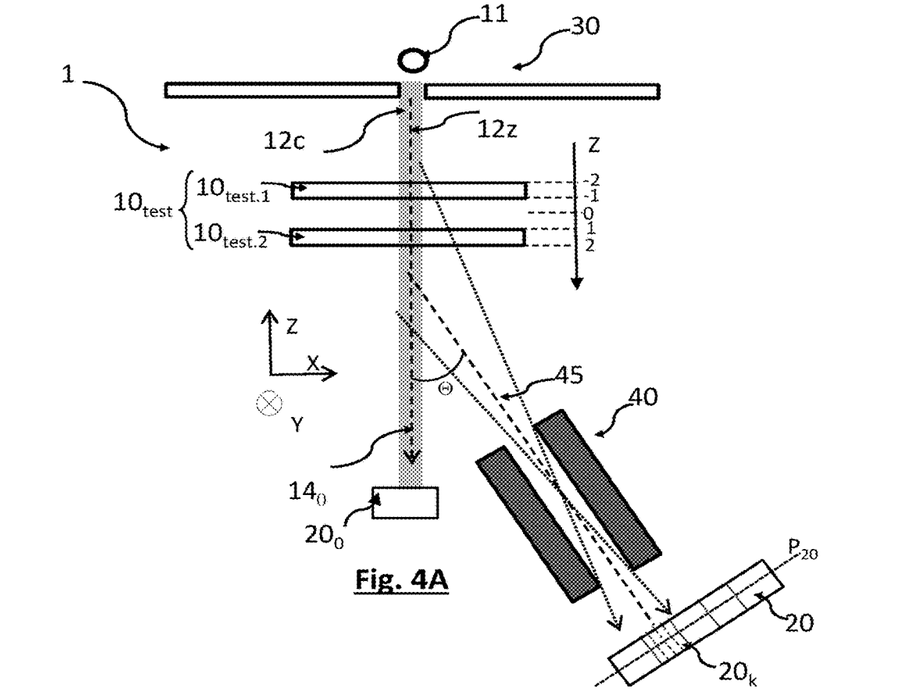
FIG. 4A shows an experimental device employing a test object.

A trial, performed on the basis of simulations, was carried out using a test object $10_{test}$ consisting of a copper plate $10_{test-1}$ of 1 cm thickness and an aluminium plate $10_{test-2}$ of 1 cm thickness, these two plates being spaced apart by 2 cm. The collimating angle $\Theta$ was here equal to 5°. The simulated device is shown in FIG. 4A.

The reference measurements $f_{k,ref}^\chi$ and $\text{Att}_{ref}$ allowing the scattering functions $f_k^\chi$ of each pixel to be obtained (cf. step 140), were carried out using a block of Plexiglas of 10 cm thickness.

Firstly, the block of Plexiglas was put in place and then, using the auxiliary detector $20_0$, a transmission spectrum $S_{0,ref}^E$ was determined. This auxiliary detector also allowed a spectrum $S_{inc}$ of the collimated incident beam $12_c$ to be measured with no object placed between the auxiliary detector $20_0$ and the first collimator 30. An attenuation spectral function $\text{Att}_{ref}$ of the reference material was thus obtained on the basis of a ratio between $S_{0,ref}^E$ and $S_{inc}$ according to Equation (16).

Figure 4B:
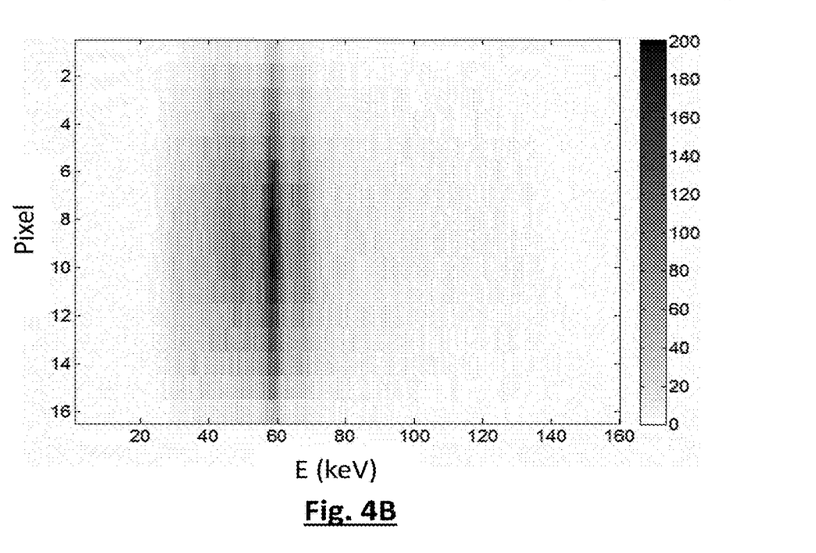
FIG. 4B shows various scattering spectra acquired by various virtual pixels and obtained with a reference material, Plexiglas in this instance.

The spectrum $S_{k,ref}^E$ of the radiative scatter of the reference material, in this instance Plexiglas, was also determined for various virtual pixels $20_k$. FIG. 4B shows these various spectra. In this figure, the x-axis represents the energy and the y-axis represents the reference of each virtual pixel, the colour code representing the amplitude of the spectrum. Each line in this figure represents the spectrum acquired by each pixel, the intensity being indicated on a greyscale.

Next, the attenuation spectral function Att of the test object $10_{test}$ was determined by measuring, with the auxiliary detector $20_0$, a spectrum with and without the test object, so as to respectively acquire the spectra $S_0^E$ and $S_{inc}$, the ratio of which allows this attenuation spectral function Att to be established, according to Expression (15).

Figure 4C:
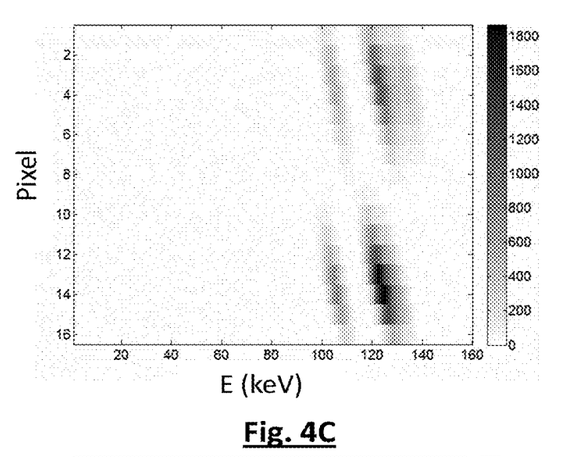
FIG. 4C shows various scattering spectra acquired by various virtual pixels during an experimental trial employing the test object.

The scattering spectra $S_k^E$ of the test object were then acquired by the various virtual pixels $20_k$, these spectra being shown in FIG. 4C. In this figure, the x-axis represents the energy and the y-axis represents the reference of each virtual pixel, the intensity being indicated on a greyscale.

For each pixel, the scattering spectrum of the object g was then normalised according to Equation (7), using the scattering spectrum of the reference object $S_{k,ref}^E$ so as to obtain, for each pixel $20_k$, a normalised spectrum $S'_k{}^E$.

Figure 4D:
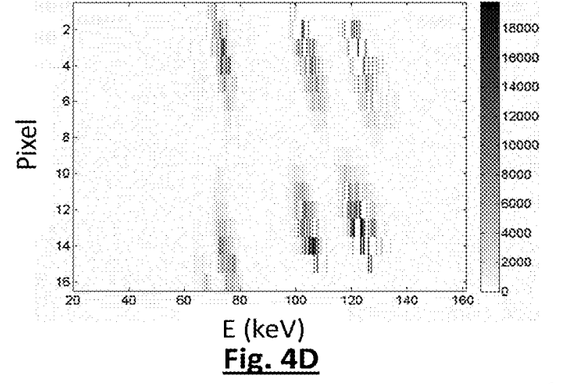
FIGS. 4D and 4E show scattering functions measured by various pixels, said functions being expressed as a function of energy or as a function of momentum transfer, respectively.
Figure 4E:
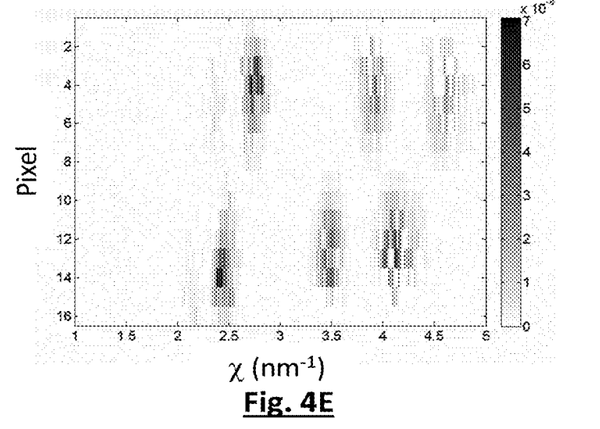

The scattering functions $f_k^{\copyright}$ of each pixel $20_k$, which functions were expressed as a function of momentum transfer $\chi$ (cf. Equation 8), were obtained from each normalised spectrum $S'_k{}^E$, using the reference-material scattering functions $f_{k,ref}^{\chi}$ associated with each pixel. FIGS. 4D and 4E respectively show the scattering functions $f_k^E$ and $f_k^{\chi}$ respectively expressed as a function of energy and ofH momentum transfer. The intensity is indicated on a greyscale.

Figure 4F:
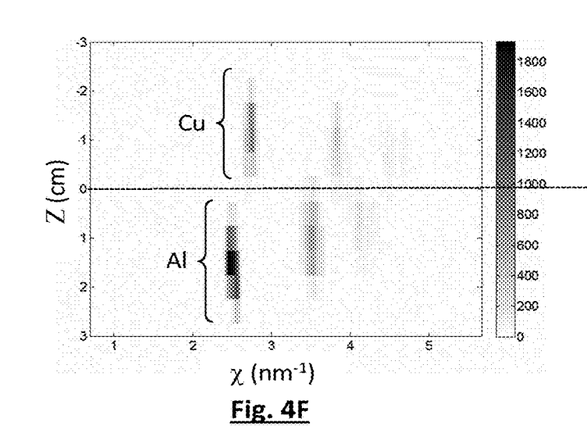
FIG. 4F shows the scattering signatures of various elementary volumes, said signatures being obtained using the scattering functions illustrated in FIG. 4E.

Knowing the dispersion matrix G, the scattering signature $f_Z^{\chi}$ of various elementary volumes distributed, in the object, along the propagation axis $12_z$ was obtained by applying Equations (9) and (10). The scattering signatures are plotted in FIG. 4F, the coordinate z=0 designating the centre of the test object. The specific signatures of aluminium (Al) and copper (Cu) were indeed obtained. This dispersion matrix was established experimentally, as described above.

Figure 4G:
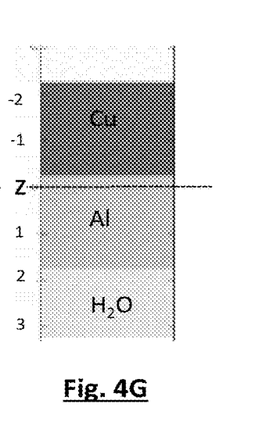
FIG. 4G illustrates the various materials identified in the test object.

FIG. 4G illustrates the various materials finally determined as a function of the coordinate z. Copper and aluminium are correctly identified. The air gap between the two materials was not identified, the space between the aluminium and the copper either being identified as being occupied by aluminium, or by copper. The presence of water at one end of the object was a result of an edge effect.

The invention will possibly be implemented in non-destructive testing applications or to assist with medical diagnoses, either a collimator including a single channel, as described in the detailed description, or a collimator including a plurality of channels being employed.

The invention claimed is:

1. A Method for analysing an object comprising:
   a) placing the object facing an irradiation source emitting ionising electromagnetic radiation and irradiating the object using the irradiation source, through a first collimator, so as to form a collimated incident beam propagating towards the object along a propagation axis;
   b) placing a detector comprising a plurality of pixels, so that each pixel is configured to detect radiation scattered by the object thus irradiated, the scattered radiation propagating in a direction making an acute scattering angle to the propagation axis;
   c) acquiring, with a plurality of pixels of the detector, a scattering spectrum representative of an energy distribution of the scattered radiation, each scattering spectrum being associated with one pixel;
   d) decomposing the object into elementary volumes and associating, with each pixel, a spatial dispersion function representing a contribution of each elementary volume to the scattered radiation detected by each pixel;
   e) on the basis of the acquired scattering spectra and of the spatial dispersion functions associated with respective pixels, determining a scattering signature associated with each elementary volume, the signature being representative of a material forming the elementary volume; and
   f) on the basis of the scattering signatures associated with each elementary volume, estimating a nature of the material forming the various elementary volumes of the object;
   wherein:
   a second collimator is interposed between the object and the detector, the second collimator defining an aperture extending between the object and the detector, along a median axis that is inclined with respect to the propagation axis, so that at least one elementary volume emits scattered radiation, through the aperture, towards various pixels of the plurality of pixels;
   the method comprises determining, for each pixel, a spatial dispersion function;
   each spatial dispersion function being established with respect to elementary volumes; and
   each spatial dispersion function representing an intensity of radiation, reaching the pixel, the radiation being respectively scattered by the elementary volumes.

2. The Method according to claim 1, wherein e) comprises, on the basis of the scattering spectrum acquired by each pixel, determining a scattering function associated with the pixel, the scattering function being obtained by combining the scattering spectrum with a reference spectrum acquired by the pixel while a reference material is placed in the place of the object.

3. The Method according to claim 2, wherein determining the scattering function associated with each pixel comprises taking into account a reference scattering function, which is established, for each pixel, relatively to the reference material.

4. The Method according to claim 3, wherein determining the scattering function associated with each pixel comprises:
   establishing a ratio, term by term, of the scattering spectrum, acquired by the pixel, to the reference spectrum, and
   multiplying, term by term, the ratio by the reference scattering function established for the pixel.

5. The Method according to claim 2, wherein e) comprises taking into account an attenuation spectral function of the object and an attenuation spectral function of the reference object.

6. The Method according to claim 2, wherein e) comprises:
   establishing a response matrix with the spatial scattering functions associated with each pixel;
   establishing a spatial dispersion matrix on the basis of with the spatial dispersion functions associated with each pixel; and
   estimating a matrix of the scattering signatures of each elementary volume, wherein a product of the spatial dispersion matrix by the matrix of scattering signatures of each elementary volume substantially corresponds to the response matrix.

7. The Method according to claim 1, wherein the spatial dispersion function associated with each pixel is elaborated by
placing a calibration object successively in various positions, along the propagation axis; and
carrying out, in each position:
i) irradiating the calibration object and acquiring, with said pixel, a calibration spectrum, of the radiation scattered by said calibration object placed in the position;
ii) in each calibration spectrum, identifying a calibration peak that is characteristic of the calibration object; and
iii) determining the intensity of the calibration peak;
the spatial dispersion function being obtained from the intensities of the calibration peaks respectively determined, for the pixel, in each position of the calibration object.

8. The Method according to claim 1, wherein f) comprises, for each elementary volume, comparing the scattering signature, obtained in e), associated with the elementary volume with pre-established scattering signatures, each pre-established scattering signatures corresponding to a known material.

9. The Method according to claim 1, wherein the pixels are virtual pixels obtained by a sub-pixelation of physical pixels of the detector.

10. A processor-readable data storage medium comprising instructions for executing d) to f) of a method according to claim 1, on the basis of scattering spectra respectively acquired by pixels of a detector, each scattering spectrum being representative of an energy distribution of a scattered radiation, each scattering spectrum being associated with one pixel.

11. A Device for analysing an object comprising:
an irradiation source, configured to produce ionising electromagnetic radiation propagating towards a holder of the object;
a first collimator, placed between the irradiation source and the holder, the first collimator having an aperture configured to form a collimated beam propagating along a propagation axis, towards the holder; and
a second collimator, placed between the holder and a detector, the second collimator having an aperture extending between the holder and the detector, along a median axis that is inclined with respect to the propagation axis;
the detector comprising pixels, each pixel being configured to detect electromagnetic radiation scattered by the object through the aperture, and to acquire a scattering spectrum;
wherein
the device comprises a microprocessor configured to carry out, on the basis of the scattering spectrum acquired by each pixel, steps d) to f) of the method according to claim 1.

12. The Device according to claim 11, wherein the median axis makes a collimating angle, to the propagation axis, the collimating angle being strictly larger than 0° and smaller than 20°.

13. The Device according to claim 11, comprising an auxiliary detector configured to acquire a transmission spectrum of radiation transmitted by the object, held on the holder, along the propagation axis.

* * * * *